United States Patent
Constantine et al.

(10) Patent No.: US 10,596,101 B2
(45) Date of Patent: Mar. 24, 2020

(54) LATHERING BATHING COMPOSITION

(71) Applicant: COSMETIC WARRIORS LIMITED, Poole, Dorset (GB)

(72) Inventors: Mark Constantine, Poole (GB); Margaret Joan Constantine, Poole (GB); Helen Elizabeth Ambrosen, Wimborne (GB); Rowena Jacqueline Bird, Christchurch (GB); Jack Constantine, Poole (GB)

(73) Assignee: COSMETIC WARRIORS LIMITED, Poole, Dorset (GB)

( * ) Notice: Subject to any disclaimer, the term of this patent is extended or adjusted under 35 U.S.C. 154(b) by 0 days.

(21) Appl. No.: 15/568,422

(22) PCT Filed: Apr. 21, 2016

(86) PCT No.: PCT/GB2016/051101
§ 371 (c)(1),
(2) Date: Oct. 20, 2017

(87) PCT Pub. No.: WO2016/170335
PCT Pub. Date: Oct. 27, 2016

(65) Prior Publication Data
US 2018/0140534 A1    May 24, 2018

(30) Foreign Application Priority Data
Apr. 22, 2015 (GB) .................................. 1506829.9

(51) Int. Cl.
| | | |
|---|---|---|
| *A61K 8/92* | (2006.01) | |
| *A61K 8/19* | (2006.01) | |
| *A61K 8/365* | (2006.01) | |
| *A61K 8/02* | (2006.01) | |
| *A61Q 19/10* | (2006.01) | |
| *A61K 8/39* | (2006.01) | |
| *A61Q 19/00* | (2006.01) | |

(52) U.S. Cl.
CPC ............ *A61K 8/922* (2013.01); *A61K 8/0216* (2013.01); *A61K 8/19* (2013.01); *A61K 8/365* (2013.01); *A61K 8/39* (2013.01); *A61Q 19/007* (2013.01); *A61Q 19/10* (2013.01); *A61K 2800/222* (2013.01)

(58) Field of Classification Search
None
See application file for complete search history.

(56) References Cited

U.S. PATENT DOCUMENTS

| | | | | |
|---|---|---|---|---|
| 6,121,215 | A * | 9/2000 | Rau ...................... | A61K 8/0204 510/130 |
| 2006/0004110 | A1* | 1/2006 | Sabnis .................. | C11D 1/146 516/10 |
| 2008/0146487 | A1* | 6/2008 | O'Connor ............... | A61K 8/02 512/4 |

FOREIGN PATENT DOCUMENTS

| | | | | |
|---|---|---|---|---|
| EP | 2671615 A1 | 12/2013 | | |
| GB | 2492139 A | * 12/2012 | ............ | A61K 8/365 |
| GB | 2492139 A | 12/2012 | | |
| JP | H02-142722 A | 5/1990 | | |
| JP | H03-74321 A | 3/1991 | | |
| WO | WO-2007014601 A1 | * 2/2007 | ......... | C11D 17/0039 |
| WO | 2008/072104 A2 | 6/2008 | | |
| WO | 2011/154727 A2 | 12/2011 | | |

OTHER PUBLICATIONS

Jenkins, L; Stephens-Shauger, T.; Phillips, L.; Miguez, K.; and Greenleaf, T. Mammoth: The Story of the Canary Springs Formation, downloaded Jul. 2, 2018 from https://www.lpi.usra.edu/education/fieldtrips/2007/explorations/mammoth/index.html. (Year: 2007).*
Anonymous. "Citrus Mango Body Butter Recipe" (downloadedfrom http://wayback.archive.org/web/20100715072728/http://www.easy-armatherapy-recipes.com/body-butterrecipe on Jul. 17, 2010 (Year: 2010).*
"About Colorants" (retrieved on Jul. 4, 2018 via the Internet Archive at https://web.archive.org/web/20141022023956/https://www..elementsbathandbody.com/About-Colorants/, dated Oct. 22, 2014). (Year: 2014).*
Raehse, Machine translation of WO2007/014601 A1 by Espacenet (Year: 2007).*
International Search Report and Written Opinion for PCT/GB2016/051101, dated Jun. 15, 2016.
Search Report for British Patent Application No. 1506829.9, dated Jan. 26, 2016.
Lush Ltd, "Butterball Bath Bomb" [online], Available from: https://web.archive.org/web/20150315013311/http://www.lushusa.com/Butterball/00012,en_US,pd.html#start=7 [Archived date Mar. 15, 2015].
R. Russel, M.D., "A dissertation of the use of sea water in the diseases of the glands: particularly the scurvy, jaundice, King's-evil, leprosy, and the glandular consumption" B4 (1760).

* cited by examiner

*Primary Examiner* — Michael P Cohen
(74) *Attorney, Agent, or Firm* — Merchant & Gould P.C.

(57) ABSTRACT

A solid cosmetic product has (i) a water dispersible fat containing component including: (a) vegetable butter, vegetable oil or a mixture thereof, present in an amount of at least 35 wt. % based on the water dispersible fat containing component; and (b) an emulsifier. The solid cosmetic product also has (ii) a carbon dioxide effervescent component including: (a) a salt of carbonic acid; and (b) an acidifying agent. The water dispersible fat containing component and the carbon dioxide effervescent component are distinct from each other.

25 Claims, No Drawings

LATHERING BATHING COMPOSITION

This application is a National Stage of PCT/GB2016/051101, filed 21 Apr. 2016, which claims benefit of British Patent Application No. 1506829.9, filed 22 Apr. 2015 which applications are incorporated herein by reference. To the extent appropriate, a claim of priority is made to each of the above disclosed applications.

FIELD OF THE INVENTION

The present invention relates to a solid cosmetic product, a process for producing said product, and a product prepared by the method.

BACKGROUND TO THE INVENTION

The present invention relates to products particularly those for use in contact with the human body.

The earliest systematic exposition of the different kinds of salts and their uses including medicinal bathing was published in China in approximately 2700 BC. Hippocrates the ancient Greek physician encouraged his fellow healers to make use of salt water to heal various ailments by immersing their patients in seawater. The ancient Greeks continued this trend and in 1753 English author and physician Dr Charles Russell popularised the practice in his 'Uses of Sea Water'.

The terms 'salts' comes from their appearance being similar to the crystals of common salt. Such salts include magnesium sulphate (also known as Epsom salts), sodium chloride, sodium bicarbonate (baking soda), sodium sesquicarbonate and sodium citrate. Salts convey a myriad of beneficial qualities to a user whilst bathing, such as cleansing, softening and exfoliating the user's skin during bathing, in addition to softening the water, thereby changing the way in which surfactants and soap behave in a bath.

One of the most popular forms of the bath salt is the Bath Bomb. Bath bomb type products date from the early $20^{th}$ century, and may be considered a form of bath salt as they typically comprises at least one salt of carbonic acid, and at least one acidifying agent. When a bath bomb is placed into water, it vigorously effervesces releasing carbon dioxide. The reaction is an acid-base reaction resulting in the production of a salt, carbon dioxide and water.

The commercially available 'Butterball' product, sold by LUSH Cosmetics, comprises a carbon dioxide effervescing component together with cocoa butter. The cocoa butter melts on contact with the bathing water and creates a layer of molten cocoa butter on top of the water that can moisturise and emolliate the user's skin. There is no emulsifier present in this product, and therefore the layer of molten cocoa butter will remain on the surface of the bathing water.

The present invention seeks to provide a solid cosmetic product which provides a dose of bathing salts and emollients, with an enhanced experience for the user.

SUMMARY OF THE INVENTION

In a first aspect, there is provided a solid cosmetic product comprising
(i) a water dispersible fat containing component comprising
(a) vegetable butter, vegetable oil or a mixture thereof, present in an amount of at least 35 wt. % based on the water dispersible fat containing component; and
(b) an emulsifier;
(ii) a carbon dioxide effervescent component comprising
(a) a salt of carbonic acid; and
(b) an acidifying agent;
wherein the water dispersible fat containing component and the carbon dioxide effervescent component are distinct from each other.

In a second aspect, there is provided a process for the production of a solid cosmetic product comprising a water dispersible fat containing component and a carbon dioxide effervescent component, wherein the water dispersible fat containing component and the carbon dioxide effervescent component are distinct from each other, the process comprising the steps of:
i) preparing the water dispersible fat containing component in one or more pieces and preparing the carbon dioxide effervescent component;
(ii) (a) enveloping the one or more pieces of water dispersible fat containing component with the carbon dioxide effervescent component; or
(b) applying the one or more pieces of water dispersible fat containing component to the outside of the carbon dioxide effervescent component.

In a third aspect, there is provided a product obtained or obtainable by a process as described herein.

In a fourth aspect, there is provided a cosmetic method comprising contacting the skin of a user with a solid cosmetic product as described herein.

For ease of reference, these and further aspects of the present invention are now discussed under appropriate section headings. However, the teachings under each section are not necessarily limited to each particular section.

Advantages

In particular, it has been found that once the solid cosmetic product of the present invention is added to water (such as bathing water) the carbon dioxide effervescent component will effervesce, as seen with the majority of commercially available bath bombs. As the fat containing component comes into contact with the water the vegetable butter and/or vegetable oil will begin to disperse and produce globules of vegetable fat, which can be coloured and fragranced to enhance the user's experience. The dual effect of the carbon dioxide effervescent component effervescing and the appearance of globules of vegetable fat produces a highly appealing visual display. Furthermore, the presence of additional components may simultaneously introduce remedial and therapeutic ingredients into a bath.

The present invention relates to a solid cosmetic product comprising a water dispersible fat containing component in addition to a carbon dioxide effervescent component. The carbon dioxide effervescent component is used to encase or carry the water dispersible fat containing component, which when dispersed in water introduces a moisturising and emolliating quality to the water. In particular, the solid cosmetic product may be used in bathing water to provide a moisturising and emolliating quality to a bath, in addition to an appealing multi-sensory display.

We have found that, by changing the composition and ratios of hard and soft vegetable butter and vegetable oil in the water dispersible fat containing component, the density of the water dispersible fat containing component can be tailored to produce distinctive effects. Typically the density of vegetable fats when in a molten state is lower than that of bathing water. Therefore, the fats are able to sit on top of the water's surface. By adjusting the density of the water dispersible fat containing component, in its solid form it is able to sink or float, before melting and rising to the surface of the bathing water.

In addition, we have found that, by including an emulsifier in the water dispersible fat containing component, the emulsifier is able to emulsify the fats present in the water dispersible fat containing component in order to produce an effect wherein the water dispersible fat containing component firstly sinks in water and is then melted by the temperature of the bathing water. On melting the fat rises to the surface of the bathing water where it dissipates after a period of time.

The aforementioned processes produce visual and olfactory stimulation to the user that provides relaxation and therapeutic effects.

DETAILED DESCRIPTION

Composition

As discussed herein, in one aspect of the present invention, there is provided a solid cosmetic product comprising
  (i) a water dispersible fat containing component comprising
    (a) vegetable butter, vegetable oil or a mixture thereof, present in an amount of at least 35 wt. % based on the water dispersible fat containing component; and
    (b) an emulsifier;
  (ii) a carbon dioxide effervescent component comprising
    (a) a salt of carbonic acid; and
    (b) an acidifying agent;
    wherein the water dispersible fat containing component and the carbon dioxide effervescent component are distinct from each other.

It will be understood by one skilled in the art that the nature of a cosmetic product means that the product is not edible. Thus in a further aspect the present invention provides a non-edible solid cosmetic product comprising
  (i) a water dispersible fat containing component comprising
    (a) vegetable butter, vegetable oil or a mixture thereof, present in an amount of at least 50 wt. % based on the fat containing component; and
    (b) an emulsifier;
  (ii) a carbon dioxide effervescent component comprising
    (a) a salt of carbonic acid; and
    (b) an acidifying agent;
wherein the fat containing component and the carbon dioxide effervescent component are distinct from each other.

The solid products of the present invention are compositions which can substantially sustain their physical shape when unsupported by external means, e.g. packaging etc. Thus, they are considered to be solid, solid-like, in solid form or in solid-like form at room temperature. For the avoidance of doubt the solid product must remain substantially solid at up to 30° C.

By solid-like, it is understood that some materials are considered on a day to day basis to be solid, yet over an extremely long period of time, may alter in shape, e.g. amorphous materials such as glass etc. However, they are considered to be solid-like as, for the purpose they fulfil, they are solid.

Due to the solid form of the compositions of the present invention, external packaging is not required to maintain the shape of the composition.

The vegetable butters used in the present invention are triglycerides which are found to be solid (including solid-like, discussed above) at normal usage temperatures. For the avoidance of doubt the vegetable butter is a triglyceride which remains substantially solid at up to 30° C. It will be appreciated however that it is not a requirement that the vegetable butter have a solid fat content of 100% at normal usage temperatures. In a preferred aspect the solid fat has a solid fat content of at least 70%, preferably at least 80%, preferably at least 90%, preferably at least 95%, preferably at least 98%, preferably at least 99% at 25° C.

The composition of the present invention is typically made by moulding of the product. In a typical process, both the carbon dioxide effervescent component and the water dispersible fat containing component are prepared and contacted with each other using one of two possible methods.

In one preferred aspect the water dispersible fat containing component is in one or more distinct pieces entirely enveloped by the carbon dioxide effervescent component. In a preferred aspect the water dispersible fat containing component is a single piece entirely enveloped by the carbon dioxide effervescent component.

In one preferred aspect the water dispersible fat containing component is in one or more distinct pieces disposed on the outside of the carbon dioxide effervescent component. In one preferred aspect the water dispersible fat containing component is in multiple distinct pieces disposed on the outside of the carbon dioxide effervescent component.

The term vegetable butter is understood by one skilled in the art and means a triglyceride obtainable from vegetable source which has the consistency of a butter.

Water Dispersible Fat Containing Component

As discussed herein, the water dispersible fat containing component comprises
  (a) vegetable butter, vegetable oil or a mixture thereof, present in an amount of at least 35 wt. % based on the fat containing component; and
  (b) an emulsifier.

In a preferred aspect the vegetable butter, vegetable oil or a mixture thereof is present in an amount of at least 35 wt. % based on the water dispersible fat containing component, such as in an amount of at least 40 wt. % based on the water dispersible fat containing component, such as in an amount of at least 45 wt. % based on the water dispersible fat containing component, such as in an amount of at least 50 wt. % based on the water dispersible fat containing component, such as in an amount of at least 55 wt. % based on the water dispersible fat containing component, such as in an amount of at least 60 wt. % based on the water dispersible fat containing component, such as in an amount of at least 65 wt % based on the water dispersible fat containing component, such as in an amount of at least 70 wt. % based on the water dispersible fat containing component.

The term vegetable butter is understood by one skilled in the art and means a triglyceride obtainable from vegetable source which has the consistency of butter.

In one aspect the vegetable butter is one or more hard vegetable butters, one or more soft vegetable butters or mixtures thereof. The term hard vegetable butter is understood by one skilled in the art and means a high saturated vegetable butter selected from vegetable butters having greater than 60 wt. % saturated fatty acids based on the total fatty acids of the high saturated vegetable butter. The term soft vegetable butter is understood by one skilled in the art and means a low saturated vegetable butter selected from vegetable butters having less than 60 wt. % saturated fatty acids based on the total fatty acids of the low saturated vegetable butter.

The one or more hard vegetable butters (also known as and referred to as high saturated vegetable butters) is preferably selected from Cocoa butter, Illipe butter, Murumuru butter, Kokum butter and mixtures thereof. In highly preferred aspect, the one or more hard vegetable butters is Cocoa butter.

The one or more soft vegetable butters (also known as and referred to as low saturated vegetable butters) is preferably selected from Aloe butter, Avocado butter, Cupuacu butter, Macadamia Nut butter, Mango butter, Olive butter, Shea butter, Coconut butter, Pumpkin Seed butter, Peanut butter, Almond butter, Coffee Bean butter, Refined butter, Hemp Seed butter, Mochacchino butter, Pistachio Nut butter, Shealoe butter and mixtures thereof. In a highly preferred aspect, the one or more soft vegetable butters is Shea butter.

In a preferred aspect, the water dispersible fat containing component comprises a hard vegetable butter. Preferably the hard vegetable butter is present in an amount of from 20 to 80 wt. % based on the water dispersible fat containing component, such as in an amount of from 25 to 75 wt. % based on the water dispersible fat containing component, such as in an amount of from 30 to 70 wt. % based on the water dispersible fat containing component, such as in an amount of from 30 to 65 wt. % based on the water dispersible fat containing component, such as in an amount of 35 to 65 wt. % based on the water dispersible fat containing component, such as in an amount of from 40 to 65 wt. % based on the water dispersible fat containing component, such as in an amount of from 45 to 65 wt. % based on the water dispersible fat containing component, such as in an amount of from 45 to 60 wt. % based on the water dispersible fat containing component, such as in an amount of from 50 to 60 wt. % based on the water dispersible fat containing component.

In a preferred aspect, the water dispersible fat containing component comprises a soft vegetable butter. Preferably the soft vegetable butter is present in an amount of from 1 to 50 wt. % based on the water dispersible fat containing component, such as in an amount of from 5 to 45 wt. % based on the water dispersible fat containing component, such as in an amount of from 5 to 40 wt. % based on the water dispersible fat containing component, such as in an amount of from 5 to 35 wt. % based on the water dispersible fat containing component, such as in an amount of from 10 to 30 wt. % based on the water dispersible fat containing component, such as in an amount of from 10 to 25 wt. % based on the water dispersible fat containing component, such as in an amount of from 10 to 20 wt. % based on the water dispersible fat containing component.

In a preferred aspect the water dispersible fat containing component comprises a mixture of hard vegetable butter and soft vegetable butter.

Preferably the hard vegetable butter and soft vegetable butter are present in a weight ratio of from 95:5 to 40:60, preferably in a weight ratio of from 90:10 to 45:55, preferably in a weight ratio of from 80:20 to 50:50, preferably in a weight ratio of from 75:25 to 55:45, preferably in a weight ratio of from 75:25 to 60:40, preferably in a weight ratio of from 75:25 to 65:35.

Preferably the hard vegetable butter is present in an amount of from 30 to 65 wt. % based on the water dispersible fat containing component, and the soft vegetable butter is present in an amount of from 5 to 35 wt. % based on the water dispersible fat containing component. Preferably the hard vegetable butter is present in an amount of from 40 to 65 wt. % based on the water dispersible fat containing component, and the soft vegetable butter is present in an amount of from 10 to 35 wt. % based on the water dispersible fat containing product. Preferably the hard vegetable butter is present in an amount of from 45 to 60 wt. % based on the water dispersible fat containing component, and the soft vegetable butter is present in an amount of from 15 to 30 wt. % based on the fat containing component.

Thus in one preferred aspect the water dispersible fat containing component comprises a vegetable butter selected from Cocoa butter, Illipe butter, Murumuru butter, Kokum butter and mixtures thereof, in an amount of 30 to 65 wt. % based on the water dispersible fat containing component, and a vegetable butter selected from Aloe butter, Avocado butter, Cupuacu butter, Macadamia Nut butter, Mango butter, Olive butter, Shea butter, Coconut butter, Pumpkin Seed butter, Peanut butter, Almond butter, Coffee Bean butter, Refined butter, Hemp Seed butter, Mochacchino butter, Pistachio Nut butter, Shealoe butter and mixtures thereof, in an amount of 5 to 35 wt. % based on the water dispersible fat containing component.

In one preferred aspect the outer layer comprises Cocoa butter in an amount of 30 to 65 wt. % based on the outer layer, and Shea butter in an amount of 5 to 35 wt. % based on the outer layer.

In a preferred aspect the water dispersible fat containing component comprises a vegetable oil. Preferably, the vegetable oil is present in an amount of from 0.001 to 20 wt. % based on the water dispersible fat containing component, such as in an amount of from 0.001 to 15 wt. % based on the water dispersible fat containing component, such as in an amount of from 0.001 to 10 wt. % based on the water dispersible fat containing component, such as in an amount of from 0.1 to 10 wt. % based on the water dispersible fat containing component, such as in an amount of 0.1 to 5 wt. % based on the water dispersible fat containing component, such as in an amount of from 1 to 5 wt. % based on the water dispersible fat containing component.

Preferably the vegetable oil is selected from almond oil, jojoba oil, castor oil, olive oil, grape seed oil, argan oil, moringa oil, baobab oil, rosehip oil, kalahari melon oil, brazil nut oil and mixtures thereof.

In a preferred aspect the water dispersible fat containing component comprises a mixture of vegetable butter and vegetable oil. In a highly preferred aspect the water dispersible fat containing component comprises a mixture of hard vegetable butter, soft vegetable butter, and vegetable oil.

In one aspect the emulsifier is present in the water dispersible fat containing component in an amount of from 1 to 30 wt. % based on the water dispersible fat containing component, such as in an amount of from 1.5 to 25 wt. % based on the water dispersible fat containing component, such as in an amount of from 2 to 20 wt. % based on the water dispersible fat containing component, such as in an amount of from 2.5 to 15 wt. % based on the water dispersible fat containing component, such as in an amount of from 2.5 to 10 wt. % based on the water dispersible fat containing component, such as in an amount of from 5 to 10 wt. % based on the water dispersible fat containing component.

In a preferred aspect the emulsifier is selected from polyoxyether of lauryl alcohol, PEG-6 caprylic/capric glycerides, PEG-60 almond glycerides, sodium cocoamphoacetate, polyglycerol-3-stearate, and mixtures thereof. An example of a suitable emulsifier is a mixture of PEG-6 caprylic/capric glycerides and PEG-60 almond glycerides. In a preferred aspect, the emulsifier is polyglycerol-3-stearate.

Thus in a preferred aspect the water dispersible fat containing component comprises
(i) hard vegetable butter in an amount of from 30 to 65 wt. % based on the water dispersible fat containing component,
(ii) soft vegetable butter in an amount of from 5 to 35 wt. % based on the water dispersible fat containing component,
(iii) vegetable oil in an amount of from 0.1 to 5 wt. % based on the water dispersible fat containing component, and
(iv) an emulsifier in an amount of from 1.5 to 25 wt. % based on the water dispersible fat containing component.

The essential components of the water dispersible fat containing component are defined herein. However the composition may contain further additional components. For example, the water dispersible fat containing component may contain one or more additional vegetable butters that are not specified herein.

In a preferred aspect the water dispersible fat containing component further comprises a colouring. Preferably, the colouring is an oil soluble colouring. In one aspect, the colouring is a water soluble colouring. Preferably, the colouring is a combination of oil soluble and water soluble colouring. An advantageous effect is achieved by combining oil soluble and water soluble colourants in the water dispersible fat containing component. In this aspect embodiment the bathing water can be coloured by a water soluble colourant present in the carbon dioxide effervescent component. When the water dispersible fat containing component is dispersed in the bathing water, the oil soluble and water soluble colourants are dispersed and a colour change is observed in the water. This is due to the blending of two separate water colourants sourced from the water dispersible fat containing component and the carbon dioxide effervescent component.

The colouring can be naturally derived or it can be synthetic.

Preferably the water dispersible fat containing component comprises colouring in an amount of from 0.001 to 5 wt. % based on the water dispersible fat containing component, such as in an amount of from 0.001 to 4 wt. % based on the water dispersible fat containing component, such as in an amount of from 0.001 to 3 wt. % based on the water dispersible fat containing component, such as in an amount of from 0.001 to 2 wt. % based on the water dispersible fat containing component, such as in an amount of from 0.1 to 2 wt. % based on the water dispersible fat containing component, such as in an amount of from 1 to 2 wt. % based on the water dispersible fat containing component.

In a preferred aspect the water dispersible fat containing component further comprises a fragrance. Preferably the fragrance is selected from essential oils. Preferably the fragrance, and more preferably the essential oil, is present in the water dispersible fat containing component in an amount of from 0.001 to 10 wt. % based on the water dispersible fat containing component, such as in an amount of from 0.001 to 8 wt. % based on the water dispersible fat containing component, such as in an amount of from 0.001 to 5 wt. % based on the water dispersible fat containing component, such as in an amount of from 1 to 5 wt. % based on the water dispersible fat containing component, such as in an amount of from 2 to 4 wt. % based on the water dispersible fat containing component.

In a preferred aspect the water dispersible fat containing component further comprises a salt of carbonic acid. Preferably the salt of carbonic acid is sodium carbonate, sodium bicarbonate or mixtures thereof. Preferably the salt of carbonic acid is sodium bicarbonate.

Preferably the water dispersible fat containing component comprises a salt of carbonic acid, and more preferably sodium bicarbonate, in an amount of from 0.001 to 30 wt. % based on the water dispersible fat containing component, such as in an amount of from 0.001 to 20 wt. % based on the water dispersible fat containing product, such as in an amount of 1 to 20 wt. % based on the water dispersible fat containing product, such as in an amount of 5 to 15 wt. % based on the water dispersible fat containing product.

Carbon Dioxide Effervescent Component

As discussed herein, the carbon dioxide effervescent component comprises
(a) a salt of carbonic acid; and
(b) an acidifying agent.

The salt of carbonic acid and the acidifying agent are present in any suitable amounts to achieve effervescence. One skilled in the art is able to combine these materials to provide the desired rate of effervescence.

Preferably the salt of carbonic acid and the acidifying agent are present in a weight ratio of from 95:5 to 50:50, preferably in a weight ratio of from 90:10 to 50:50, preferably in a weight ratio of from 90:10 to 55:45, preferably in a weight ratio of from 90:10 to 60:40, preferably in a weight ratio of from 90:10 to 70:30.

In one aspect the carbon dioxide effervescent component comprises a salt of carbonic acid selected from alkali metal carbonates, alkali metal bicarbonates and mixtures thereof.

Preferably, the salt of carbonic acid is selected from sodium bicarbonate, sodium carbonate and mixtures thereof.

In a preferred aspect the carbon dioxide effervescent component comprises the salt of carbonic acid, and preferably sodium bicarbonate, in an amount of from 40 to 95 wt % based on the carbon dioxide effervescent component. In a preferred aspect the carbon dioxide effervescent component comprises the salt of carbonic acid, and preferably sodium bicarbonate, in an amount of from 45 to 95 wt. % based on the carbon dioxide effervescent component. In a preferred aspect the carbon dioxide effervescent component comprises the salt of carbonic acid, and preferably sodium bicarbonate, in an amount of from 50 to 95 wt. % based on the carbon dioxide effervescent component. In a preferred aspect the carbon dioxide effervescent component comprises the salt of carbonic acid, and preferably sodium bicarbonate, in an amount of from 50 to 90 wt. % based on the carbon dioxide effervescent component. In a preferred aspect the carbon dioxide effervescent component comprises the salt of carbonic acid, and preferably sodium bicarbonate, in an amount of from 55 to 90 wt. % based on the carbon dioxide effervescent component. In a preferred aspect the carbon dioxide effervescent component comprises the salt of carbonic acid, and preferably sodium bicarbonate, in an amount of from 60 to 85 wt. % based on the carbon dioxide effervescent component. In a preferred aspect the carbon dioxide effervescent component comprises the salt of carbonic acid, and preferably sodium bicarbonate, in an amount of from 60 to 80 wt. % based on the carbon dioxide effervescent component. In a preferred aspect the carbon dioxide effervescent component comprises the salt of carbonic acid, and preferably sodium bicarbonate, in an amount of from 60 to 75 wt. % based on the carbon dioxide effervescent component.

In one aspect the carbon dioxide effervescent component comprises an acidifying agent selected from monocarboxylic acids, dicarboxylic acids, tricarboxylic acids and mixtures thereof.

Preferably the acidifying agent is selected form citric acid, potassium bitartrate (cream of tartar) and mixtures thereof. In a preferred aspect the carbon dioxide effervescent component comprises the acidifying agent, and preferably citric acid, in an amount of from 5 to 60 wt. % based on the carbon dioxide effervescent component. In a preferred aspect the carbon dioxide effervescent component comprises the acidifying agent, and preferably citric acid, in an amount of from 5 to 55 wt. % based on the carbon dioxide effervescent component. In a preferred aspect the carbon dioxide effervescent component comprises the acidifying agent, and preferably citric acid, in an amount of from 5 to 50 wt. % based on the carbon dioxide effervescent component. In a preferred aspect the carbon dioxide effervescent component comprises the acidifying agent, and preferably citric acid, in an amount of from 5 to 45 wt. % based on the carbon dioxide effervescent component. In a preferred aspect the carbon dioxide effervescent component comprises the acidifying agent, and preferably citric acid, in an amount of from 5 to 40 wt. % based on the carbon dioxide effervescent component. In a preferred aspect the carbon dioxide effervescent component comprises the acidifying agent, and preferably citric acid, in an amount of from 5 to 35 wt. % based on the carbon dioxide effervescent component. In a preferred aspect the carbon dioxide effervescent component comprises the acidifying agent, and preferably citric acid, in an amount of from 5 to 30 wt. % based on the carbon dioxide effervescent component.

In a preferred aspect the carbon dioxide effervescent component comprises sodium bicarbonate in an amount of from 55 to 90 wt. % and citric acid in an amount of from 5 to 40 wt. % based on the carbon dioxide effervescent component.

The essential components of the carbon dioxide effervescent component are defined herein. However the composition may contain further additional components.

In a preferred aspect the carbon dioxide effervescent component further comprises a colouring. Preferably, the colouring is a water soluble colouring. The colouring can be naturally derived or it can be synthetic.

Preferably the carbon dioxide effervescent component comprises colouring in an amount of from 0.001 to 5 wt. % based on the carbon dioxide effervescent component, such as in an amount of from 0.001 to 4 wt. % based on the carbon dioxide effervescent component, such as in an amount of from 0.001 to 3 wt. % based on the carbon dioxide effervescent component, such as in an amount of from 0.001 to 2 wt. % based on the carbon dioxide effervescent component, such as in an amount of from 0.1 to 2 wt. % based on the carbon dioxide effervescent component, such as in an amount of from 1 to 2 wt. % based on the carbon dioxide effervescent component.

In a preferred aspect the carbon dioxide effervescent component further comprises a fragrance. Preferably the fragrance is selected from essential oils. Preferably the fragrance, and more preferably the essential oil, is present in the carbon dioxide effervescent component in an amount of from 0.001 to 10 wt. % based on the carbon dioxide effervescent component, such as in an amount of from 0.001 to 8 wt. % based on the carbon dioxide effervescent component, such as in an amount of from 0.001 to 5 wt. % based on the carbon dioxide effervescent component, such as in an amount of from 1 to 5 wt. % based on the carbon dioxide effervescent component, such as in an amount of from 2 to 4 wt. % based on the carbon dioxide effervescent component.

In one aspect the carbon dioxide effervescent component comprises a vegetable oil. Preferably, the vegetable oil is present in an amount of from 0.001 to 10 wt. % based on the carbon dioxide effervescent component, such as in an amount of from 0.1 to 10 wt. % based on the carbon dioxide effervescent component, such as in an amount of 0.1 to 5 wt. % based on the carbon dioxide effervescent component, such as in an amount of from 1 to 5 wt. % based on carbon dioxide effervescent component.

Preferably the vegetable oil is selected from almond oil, jojoba oil, castor oil, olive oil, grape seed oil, argan oil and mixtures thereof.

Water Dispersible Fat Containing Component & Carbon Dioxide Effervescent Component The water dispersible fat containing component and the carbon dioxide effervescent component may be present in suitable relevant amounts to provide the desired properties for the product. In one aspect, the water dispersible fat containing component is 2 to 50 wt. % and the carbon dioxide effervescent component is 50 to 98 wt %, based on the combined weight of the water dispersible fat containing component and the carbon dioxide effervescent component. Preferably, the water dispersible fat containing component is 5 to 50 wt. % and the carbon dioxide effervescent component is 50 to 95 wt. % based on the combined weight of the water dispersible fat containing component and the carbon dioxide effervescent component. Preferably, the water dispersible fat containing component is 10 to 50 wt. % and the carbon dioxide effervescent component is 50 to 90 wt %, based on the combined weight of the water dispersible fat containing component and the carbon dioxide effervescent component. Preferably, the water dispersible fat containing component is 10 to 40 wt. % and the carbon dioxide effervescent component is 60 to 90 wt. % based on the combined weight of the water dispersible fat containing component and the carbon dioxide effervescent component. Preferably, the water dispersible fat containing component is 10 to 30 wt. % and the carbon dioxide effervescent component is 70 to 90 wt. %, based on the combined weight of the water dispersible fat containing component and the carbon dioxide effervescent component.

In one aspect the water dispersible fat containing component is in one or more distinct pieces entirely enveloped by the carbon dioxide component. Preferably the water dispersible fat containing component is in a single piece entirely enveloped by the carbon dioxide effervescent component.

In one aspect the water dispersible fat containing component is in one or more distinct pieces disposed on the outside of the carbon dioxide effervescent component. Preferably the water dispersible fat containing component is in multiple distinct pieces disposed on the outside of the carbon dioxide effervescent component.

The combined amount of the water dispersible fat containing component and the carbon dioxide effervescent component in any amount to provide the desired physical characteristics of the solid cosmetic product. Preferably the combined amount of the water dispersible fat containing component and the carbon dioxide effervescent component is from about 10% to about 100% by weight of the total composition. Preferably the combined amount of the water dispersible fat containing component and the carbon dioxide effervescent component is from about 20% to about 100% by weight of the total composition. Preferably the combined amount of the water dispersible fat containing component and the carbon dioxide effervescent component is from about 30% to about 100% by weight of the total composition. Preferably the combined amount of the water dispersible fat containing component and the carbon dioxide effervescent component is from about 40% to about 100% by weight of the total composition. Preferably the combined amount of the water dispersible fat containing component and the carbon dioxide effervescent component is from about 50% to about 100% by weight of the total composition. Preferably the combined amount of the water dispersible fat containing component and the carbon dioxide effervescent component is from about 60% to about 100% by weight of the total composition. Preferably the combined amount of the water dispersible fat containing component and the carbon dioxide effervescent component is from about 70% to about 100% by weight of the total composition. Preferably the combined amount of the water dispersible fat containing component and the carbon dioxide effervescent component is from about 80% to about 100% by weight of the total composition. Preferably the combined amount of the water dispersible fat containing component and the carbon dioxide effervescent component is from about 85% to about 100% by weight of the total composition. Preferably the combined amount of the water dispersible fat containing component and the carbon dioxide effervescent component is from about 90% to about 100% by weight of the total composition. Preferably the combined amount of the water dispersible fat containing component and the carbon dioxide effervescent component is from about 95% to about 100% by weight of the total composition. Preferably the combined amount of the water dispersible fat containing component and the carbon dioxide effervescent component is 100% by weight of the total composition.

Each of the water dispersible fat containing component and the carbon dioxide effervescent material may optionally contain colouring independently of each other. When both materials contain colouring, the colours may be selected such that a first colour in the carbon dioxide effervescent component is dispersed in the water in use. When the water contacts the water dispersible fat containing component a second colour may be dispersed. If this second colour is different to the first colour, the user will observe globules of the second colour as globules of the water dispersible fat containing component are dispersed in the water. If the water dispersible fat containing component contains two colourings a colour change can be observed in the water in use.

Additional Components

The solid product of the present invention may also comprise one or more cosmetically acceptable additives. The person skilled in the art is aware of a range of cosmetically acceptable additives which are suitable for incorporation into such compositions. For example, binders, fillers, opacifiers, perfumes, fragrances, decorative items and mixtures thereof.

It is particularly preferred that the composition of the present invention further comprises a fragrance. Preferably the fragrance is selected from essential oils.

In a preferred aspect the water dispersible fat containing component comprises a fragrance in an amount of 0.001 to 5 wt. % based on the water dispersible fat containing component, and the carbon dioxide effervescent component comprises a fragrance in an amount of 0.001 to 5 wt. % based on the carbon dioxide effervescent component.

Fruit and herb extracts and juices, vegetable oils and essential oils are all compatible with the composition. Colours, both naturally derived and synthetic can be used to colour the product.

In one embodiment, the cosmetically acceptable additives are selected from the group consisting of essential oils, vitamins, fragrances, colourings, clays, decorative articles and mixtures thereof.

The essential oils may be selected based on the fragrance desired, skin type to be treated and other effects desired based on the well known properties of essential oils. The addition of essential oils, when taken in to the nose, are known to alter mood. For example, essential oils are known to create effects of drowsiness or stimulating the senses. Many well documented effects can be achieved by the use of essential oils.

In one embodiment, the one or more essential oils present in the solid product are selected from Tarragon, Lemon myrtle, Jasmin, Ylang ylang, Labdunum, Lemongrass, Rose otto, Grapefruit, Patchouli, Rosemary, Armois, Lemon, Neroli, Sweet violet, Lavender, Orange 50 fold, Vanilla, Peppermint, Benzoin, Hydrangia, Litsea Cubeba, Cardamon, Tonka, and Chamomile blue. In one embodiment, the one or more essential oils present in the solid product are selected from Tarragon, Lemon myrtle, Labdunum, and Lemon.

Vitamins, particularly B, C and E are very beneficial for the skin. Vitamin rich ingredients such as Wheatgerm oil can also be used to deliver vitamins on to the skin. In a one embodiment, the vitamins are selected from vitamin B, vitamin C, vitamin E and mixtures thereof. It will be appreciated by one skilled in the art that the vitamin may be provided from any suitable source. For example the vitamin(s) may be provided from a synthetic source or from incorporation into the solid product of a material, such as a natural material, that has a high vitamin content.

The ingredients in the present invention do not require cosmetic preservatives. The use of cosmetic preservatives can increase the potential to irritate the skin.

The decorative items which may be present in the solid product include items such as glitter, paper such as rice paper, sequins, dried or fresh flowers, herbs, vegetables, parts thereof or mixtures thereof. Other enhancing materials may also be incorporated Further preferred additive materials include vegetable oils, chocolate, herbs and spices, cosmetic colours (e.g. paprika, gardenia extract, D&C red no. 30), beans (e.g. aduki), fruit, fresh or dried (e.g. banana, avocado, mango, papaya, kiwi, raspberry, strawberry, blueberries, grapes, tomato, asparagus, or cucumber), honey, glycerin, cosmetic glitter, other vegetable butters (e.g. mango, avocado), clays (e.g. kaolin), starches (e.g. corn starch) and mixtures thereof.

The above ranges provide preferred amounts of each of the components. Each of these ranges may be taken alone or combined with one or more other component ranges to provide a preferred aspect of the invention.

Process

As discussed herein, the invention provides a process for the production of a solid cosmetic product as described herein;

the process comprising the steps of:

i) preparing the water dispersible fat containing component in one or more pieces and preparing the carbon dioxide effervescent component;

ii) (a) enveloping the one or more pieces of water dispersible fat containing component with the carbon dioxide effervescent component; or (b) applying the one or more pieces of water dispersible fat containing component to the outside of the carbon dioxide effervescent component.

Preferably the water dispersible fat containing component of step i) is caused to solidify in a predetermined shape. After solidification the carbon dioxide effervescent component of step i) is placed around the solid so as to envelop it as in step 1(a). The carbon dioxide effervescent component is also typically caused to solidify in a predetermined shape.

Preferably the carbon dioxide effervescent component of step i) is caused to solidify in a predetermined shape. After solidification the one or more pieces of water dispersible fat containing component of step i) are applied to the outside of the solidified carbon dioxide effervescent material as in step 1(b). The water dispersible fat containing component is then solidified to a predetermined shape.

The shape of the solid products of the present invention is not limited. It may be that the solid products are provided with a shape which would be aesthetically pleasing and/or which aids in the use of the product. For example, it may be that the solid product is produced in such a manner so that it solidifies in a shape which is ergonomically acceptable to the user. Therefore, in one embodiment of the process of the present invention, the mixture of step i) and/or step ii) is pressed into a mould, allowed to solidify, and then turned out to produce the solid product. Preferable shapes include spheres, cubes, cuboids and cones.

As described herein, the solid product may further comprise one or more cosmetically acceptable additives. In one embodiment, the process further comprises the step of combining with the mixture of step i) and/or step ii) one or more cosmetically acceptable additives as defined herein and/or the dispersant defined herein.

The present invention also provides a product obtained or obtainable by a process as described herein.

Method

In one aspect of the present invention, there is provided a method comprising contacting the skin of a user with water in which the solid cosmetic product as defined herein has been placed in, or has dissolved in, or in which the solid cosmetic product as defined herein is dissolving. In a typical method, water is run in to the bath at an acceptable temperature. The user immerses their body in the water and the solid cosmetic composition is dropped into the water. The user then watches the effect of the product on the surface of the water as the outer layer dissolves and disperses its colouring, whilst releasing the components of the inner core. The colouring of the inner core is thus dispersed through water. The user than bathes in the water.

EXAMPLES

The invention will now be described with reference to the following non-limiting examples.

A general methodology for preparing compositions in accordance with the present invention is as follows:

1. Mix together the salt of carbonic acid and an acidifying agent with any additional components, such as decorative materials, fragrance and colouring into a powdered mix.
2. Warm the vegetable butters to 50-70° C. and add any vegetable oil or colouring whilst mixing until all component parts are well incorporated.
3. Add the emulsifier and any additional components, such as fragrance or decorative items, and mix well until all the component parts are well incorporated.
4. Cool to approximately 30-40° C. and pour into moulds and leave to set.
5. Add the water dispersible fat containing component to the carbon dioxide effervescent component.
6. Leave until the composition has set and remove from the mould.

Example 1

A solid cosmetic product having the following composition was prepared. The amounts of each component part are provided as wt. % based on the fat containing component or carbon dioxide effervescent component, depending on where the component part is found in the product.

|  | Total Batch Size | 1000 g |
|---|---|---|
|  | Raw Material |  |
| Carbon Dioxide Effervescent Component | | 95.00 wt. % |
| wt % (based on component) | | wt. (g) |
| 74.00 | Sodium Bicarbonate | 703.00 |
| 22.00 | Citric Acid | 209.00 |
| 3.00 | Fragrance | 28.50 |
| 1.00 | Crocin Extract | 9.50 |
| Fat Containing Component | | 5.00 wt. % |
| wt % (based on component) | | wt. (g) |
| 61.40 | Cocoa Butter | 30.70 |
| 18.32 | Shea Butter | 9.16 |
| 11.32 | Olive Oil | 5.66 |
| 3.20 | PEG-6 caprylic/capric & PEG-60 glycerides | 1.60 |
| 2.08 | Violet No2 Powder | 1.04 |
| 3.68 | Fragrance | 1.84 |
|  |  | 1000.00 |

The product was prepared as follows:

1. The carbon dioxide effervescent component was prepared as follows—Mix the sodium bicarbonate and citric acid together with some of the colour and some of the fragrance into a powdered mix.
2. The water dispersible fat containing product was prepared as follows—Warm the vegetable butters to 60° C. and add the vegetable oil and the remaining colour whilst mixing until all component parts are well incorporated. Add the remaining fragrance and the emulsifier and mix well until all component parts are well incorporated. Cool to 30° C. and pour into moulds and leave to set.

The water dispersible fat containing component and carbon dioxide effervescent component were combined as follows 1. Once the fat containing component in the mould is sufficiently cool and hard enough to handle, place the solid fat containing component at the bottom of the mould.
2. Fill the remainder of the mould with the sodium bicarbonate and citric acid mix.
3. Leave until the composition has set.
4. Remove from the mould.

Example 2

A solid cosmetic product having the following composition was prepared. The amounts of each component part are provided as wt. % based on the fat containing component or carbon dioxide effervescent component, depending on where the component part is found in the product.

|  | Total Batch Size | 1000 g |
|---|---|---|
|  | Raw Material |  |
| Carbon Dioxide Effervescent Component | | 97.00 wt. % |
| wt % (based on component) | | wt. (g) |
| 75.00 | Sodium Bicarbonate | 727.50 |
| 23.00 | Citric Acid | 223.10 |
| 1.50 | Fragrance | 14.55 |
| 0.50 | FD&C Blue No 1 | 4.85 |
| Fat Containing Component | | 3.00 wt. % |
| wt % (based on component) | | wt. (g) |
| 63.15 | Cocoa Butter | 18.95 |
| 18.20 | Shea Butter | 5.46 |
| 14.50 | Polyglycerol-3-stearate | 4.35 |
| 2.15 | Castor Oil | 0.65 |
| 1.75 | Fragrance | 0.53 |
| 0.25 | FD&C Red No 27 | 0.08 |
|  |  | 1000.00 |

The product was prepared in accordance with the process of Example 1.

Various modifications and variations of the present invention will be apparent to those skilled in the art without departing from the scope and spirit of the invention. Although the invention has been described in connection with specific preferred embodiments, it should be understood that the invention as claimed should not be unduly limited to such specific embodiments. Indeed, various modifications of the described modes for carrying out the invention which are obvious to those skilled in chemistry, biology or related fields are intended to be within the scope of the following claims.

The invention claimed is:

1. A solid cosmetic product comprising;
   (i) a water dispersible fat containing component comprising;
      (a) vegetable butter, vegetable oil or a mixture thereof present in an amount of at least 35 wt. % based on the fat containing component; and
      (b) an emulsifier;
   (ii) a carbon dioxide effervescent component comprising:
      (a) a salt of carbonic acid; and
      (b) an acidifying agent;
   wherein the water dispersible fat containing component and the carbon dioxide effervescent component are distinct from each other,
   wherein the water dispersible fat containing component is in multiple distinct pieces disposed on the outside of the carbon dioxide effervescent component; and
   wherein a density of the water dispersible fat containing component, in a solid form, is able to sink in a bathing water, before melting due to a temperature of the bathing water, and rising to the surface of the bathing water.

2. A solid cosmetic product according to claim 1 wherein the water dispersible fat containing component is 2 to 50 wt. % and the carbon dioxide effervescent component is 50 to 98 wt %, based on a combined weight of the water dispersible fat containing component and the carbon dioxide effervescent component.

3. A solid cosmetic product according to claim 1 wherein the water dispersible fat containing component is 5 to 25 wt. % and the carbon dioxide effervescent component is 75 to 95 wt %, based on a combined weight of the water dispersible fat containing component and the carbon dioxide effervescent component.

4. A solid cosmetic product according to claim 1 wherein the water dispersible fat containing component comprises hard vegetable butter in an amount of from 30 to 65 wt. % based on the water dispersible fat containing component.

5. A solid cosmetic product according to claim 4 wherein the hard vegetable butter is selected from Cocoa butter, Illipe butter, Murumuru butter, Kokum butter and mixtures thereof.

6. A solid cosmetic product according to claim 1 wherein the water dispersible fat containing component comprises soft vegetable butter in an amount of from 5 to 35 wt. % based on the water dispersible fat containing component.

7. A solid cosmetic product according to claim 6 wherein the soft vegetable butter is selected from Aloe butter, Avocado butter, Cupuacu butter, Macadamia Nut butter, Mango butter, Olive butter, Shea butter, Coconut butter, Pumpkin Seed butter, Peanut butter, Almond butter, Coffee Bean butter, Refined butter, Hemp Seed butter, Mochacchino butter, Pistachio Nut butter, Shealoe butter and mixtures thereof.

8. A solid cosmetic product according to claim 1 wherein the emulsifier is present in an amount of from 1.5 to 25 wt % based on the water dispersible fat containing component.

9. A solid cosmetic product according to claim 1 wherein the emulsifier is selected from polyoxyether of lauryl alcohol, PEG-6 caprylic/capric glycerides, PEG-60 almond glycerides, sodium cocoamphoacetate and mixtures thereof.

10. A solid cosmetic product according to claim 1 wherein the water dispersible fat containing component further comprises a colouring.

11. A solid cosmetic product according to claim 10 wherein the water dispersible fat containing component comprises an oil soluble colouring.

12. A solid cosmetic product according to claim 10 wherein the water dispersible fat containing component comprises an oil soluble colouring and a water soluble colouring.

13. A solid cosmetic product according to claim 10 wherein the water dispersible fat containing component comprises colouring in an amount of from 0.001 to 5 wt % based on the water dispersible fat containing component.

14. A solid cosmetic product according to claim 1 wherein the salt of carbonic acid and the acidifying agent are present in a weight ratio of from 90:10 to 50:50.

15. A solid cosmetic product according to claim 1 wherein the salt of carbonic acid and the acidifying agent are present in a weight ratio of from 90:10 to 70:30.

16. A solid cosmetic product according to claim 1 wherein the salt of carbonic acid is selected from alkali metal carbonates, alkali metal bicarbonates and mixtures thereof.

17. A solid cosmetic product according to claim 1 wherein the salt of carbonic acid is selected from sodium bicarbonate, sodium carbonate and mixtures thereof.

18. A solid cosmetic product according to claim 1 wherein the acidifying agent is selected from monocarboxylic acids, dicarboxylic acids, tricarboxylic acids and mixtures thereof.

19. A solid cosmetic product according claim 1 wherein the acidifying agent is selected citric acid; potassium bitartrate and mixtures thereof.

20. A solid cosmetic product according to claim 1 wherein the carbon dioxide effervescent component comprises:
   (a) sodium bicarbonate in an amount of from 55 to 90 wt % based on the carbon dioxide effervescent component; and
   (b) citric acid in an amount of from 5 to 40 wt % based on the carbon dioxide effervescent component.

21. A solid cosmetic product according to claim 1 wherein the carbon dioxide effervescent component further comprises a colouring.

22. A solid cosmetic product according to claim 21 wherein the carbon dioxide effervescent component comprises a water soluble colouring.

23. A solid cosmetic product according to claim 21 wherein the carbon dioxide effervescent component comprises colouring in an amount of from 0.001 to 5 wt % based on the carbon dioxide effervescent component.

24. A solid cosmetic product according to claim 1 wherein the water dispersible fat containing component or the carbon dioxide effervescent component further comprises at least one additional component selected from binders, fillers, opacifiers, perfumes, fragrances, decorative items and mixtures thereof.

25. A solid cosmetic product according to claim 1 wherein the product is a bathing product.

* * * * *